United States Patent [19]
Chen

[11] Patent Number: 5,089,008
[45] Date of Patent: Feb. 18, 1992

[54] SURGICAL CLOSURE MEANS FOR ANASTOMOTIC DEVICE

[76] Inventor: Fusen H. Chen, 240 Thompson Rd., Webster, Mass. 01570

[21] Appl. No.: 629,608

[22] Filed: Dec. 18, 1990

Related U.S. Application Data

[63] Continuation-in-part of Ser. No. 472,209, Jan. 26, 1990, Pat. No. 4,997,439, which is a continuation-in-part of Ser. No. 303,326, Jan. 26, 1989, Pat. No. 4,930,502.

[51] Int. Cl.$^5$ .............................................. A61B 17/00
[52] U.S. Cl. ..................................... 606/216; 606/213
[58] Field of Search ............................... 606/213–216, 606/220, 221, 150, 151, 153

[56] References Cited

U.S. PATENT DOCUMENTS

| | | | |
|---|---|---|---|
| 3,825,010 | 7/1976 | McDonald | 606/216 |
| 4,430,998 | 2/1984 | Harvey et al. | 606/216 |
| 4,526,173 | 7/1985 | Sheehan | 606/216 |
| 4,637,380 | 1/1987 | Orejola | 606/216 |
| 4,676,245 | 6/1987 | Fukuda | 606/216 |
| 4,924,866 | 3/1990 | Yoon | 606/216 |

Primary Examiner—Stephen C. Pellegrino
Assistant Examiner—Gary Jackson
Attorney, Agent, or Firm—Morris Kaplan

[57] ABSTRACT

The structure of either elongated strips or annuli for linear or tubular surgical joiner are male and female members that lock at their distal ends; have abutting planar faces at their intermediate sections for stabilizing purposes; are configured to form a void at their proximal portions for accommodating inflammation and swelling of the surgically joined parts; and have suturing pins that are each annularly slotted at their distal ends and project from a proximal edge face of one of the members, extend through partially everted parts to be surgically joined and through securing panel means formed in the opposed proximal part of the second of the members; the panel edges releasably locking into a selected annular slot for controlling clamp pressure.

15 Claims, 7 Drawing Sheets

SURGICAL CLOSURE MEANS FOR ANASTOMOTIC DEVICE

CROSS-REFERENCE TO RELATED APPLICATIONS

This application is a continuation-in-part of allowed application Ser. No. 07/472,209, filed Jan. 26, 1990 in turn a continuation-in-part of application Ser. No. 7/303,326, filed Jan. 26, 1989, and now U.S. Pat. No. 4,930,502.

TECHNICAL FIELD

The present invention relates to the surgical joining of tubular structures and of elongated openings.

BACKGROUND OF THE INVENTION

The use of anastomotic devices for clamping and suturing is well known in the medical art. See, for instance, U.S. Pat. Nos. 2,638,901 (Sugarbaker); 3,254,650 (Collito); 4,233,981 (Schomacher); 4,294,255 (Geroc); 4,523,592 (Daniel); 4,657,019 (Walsh et al.); and 4,757,407 (Liv et al).

Also known in the medical art are devices supporting pluralities of linearly spaced pins adapted for closing or suturing elongated openings, wounds, or surgical incisions. See, for instance, U.S. Pat. Nos. 3,825,010 (McDonald); 4,430,998 (Harvey et al.); 4,526,173 (Sheehan); 4,637,380 (Orejola); 4,676,245 (Fukuda); and 4,924,866 (Yoon).

These patents are discussed in part in the referenced parent application files, the disclosures of which are hereby incorporated herein by reference.

The known prior art devices of the type are not fully satisfactory for at least some of the reasons that:

tissue swelling is not provided for;

the device comprises a clamping means that requires a relatively large contact area with the tissue or body structure;

means are not provided for controlling and locking in clamping pressure whereby to avoid excesses that may be causative of necrosis or at least result in severely diminished blood flow and a prolonged period for healing;

the device is awkward to use, in contradistinction to efficient surgical procedure; and the device is relatively sophisticated with respect to manufacture and use.

SUMMARY OF THE INVENTION

The present invention is directed to an improved surgical device that is: mechanically simple and inexpensive to manufacture; easy to use to thus facilitate efficient surgical procedure; accommodates tissue swelling; provides for minimal device to body structure area of contact; and provides positive means for adjusting clamping pressure, and for locking-in selected pressure and suturing pin orientation.

In a preferred embodiment of the improved device, whether a ring type for anastomosis or a linear type for suturing of an elongated wound or opening, novel means are provided in the form of spaced pins which each have a plurality of longitudinally spaced annular slots. Each pin extends from a first device member, is adapted to effect suturing and operatively associates with a second device member for controlling locking in an aperture defined by crisscrossing slits formed in a thinned flexible wall.

Other species of improved joinder and closure devices are disclosed.

For a more fully developed presentation of the invention, and preferred embodiments thereof, reference is made to the following descriptive matter, attached drawings, and claims.

DETAILED DESCRIPTION OF THE INVENTION

Referring to the drawings which illustrate preferred embodiments of the invention and wherein like numerals indicate like elements of structure, there is shown in FIGS. 1A–4 an anastomotic device wherein the designations A and B relate to respective male and female members or to structural elements thereof.

Figure 1A:
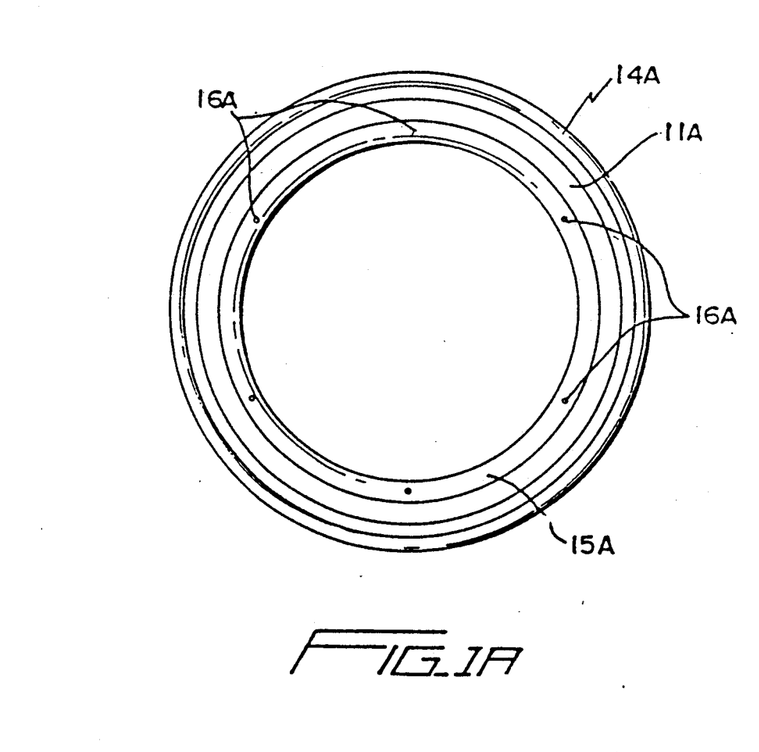
FIGS. 1A and 1B are plan views of a first embodiment of an improved anastomotic device and show the inner faces to be operatively associated.
Figure 1B:
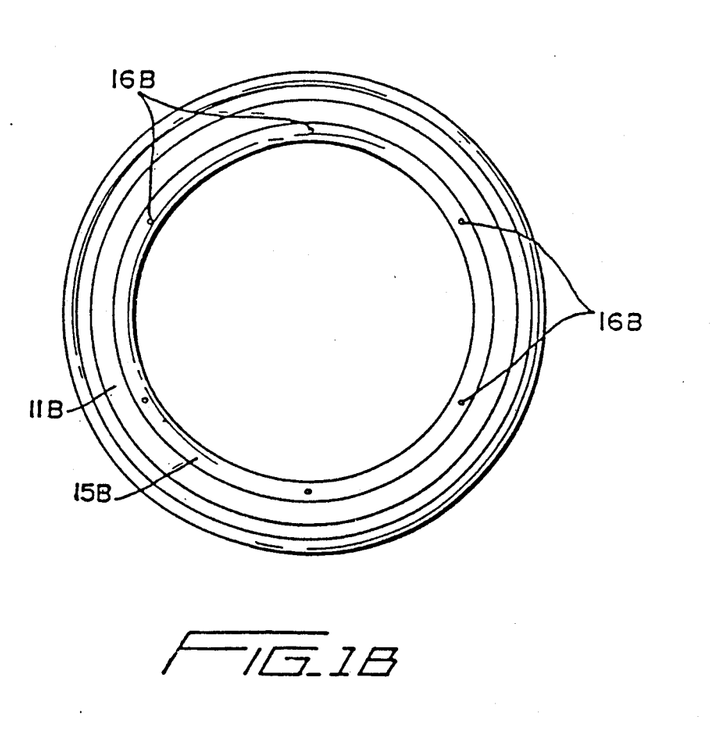
Figure 2A:
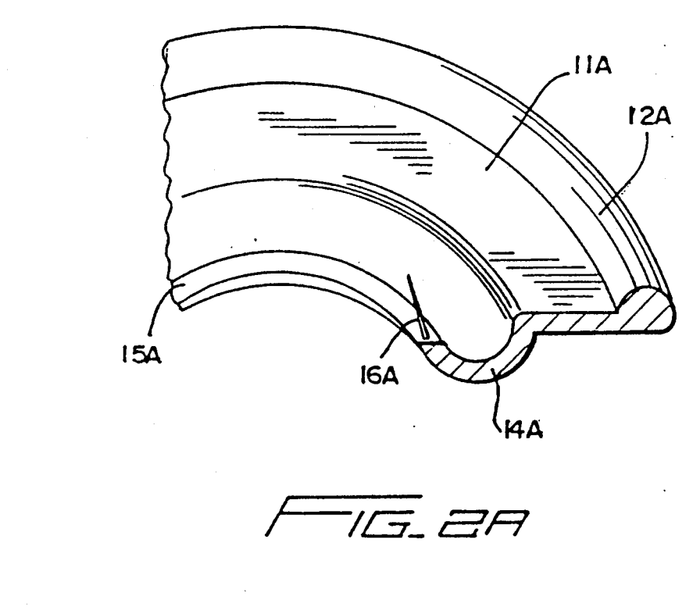
FIGS. 2A and 2B are partial perspective views corresponding to FIGS. 1A and 1B, respectively.
Figure 2B:
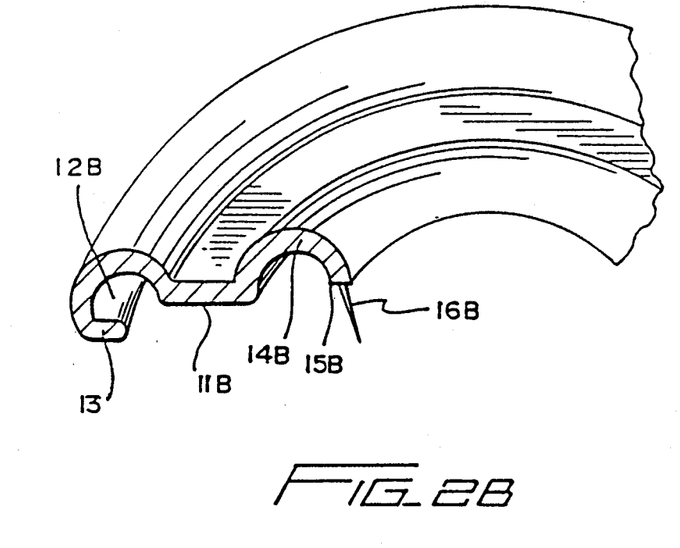
Figures 3, 4:
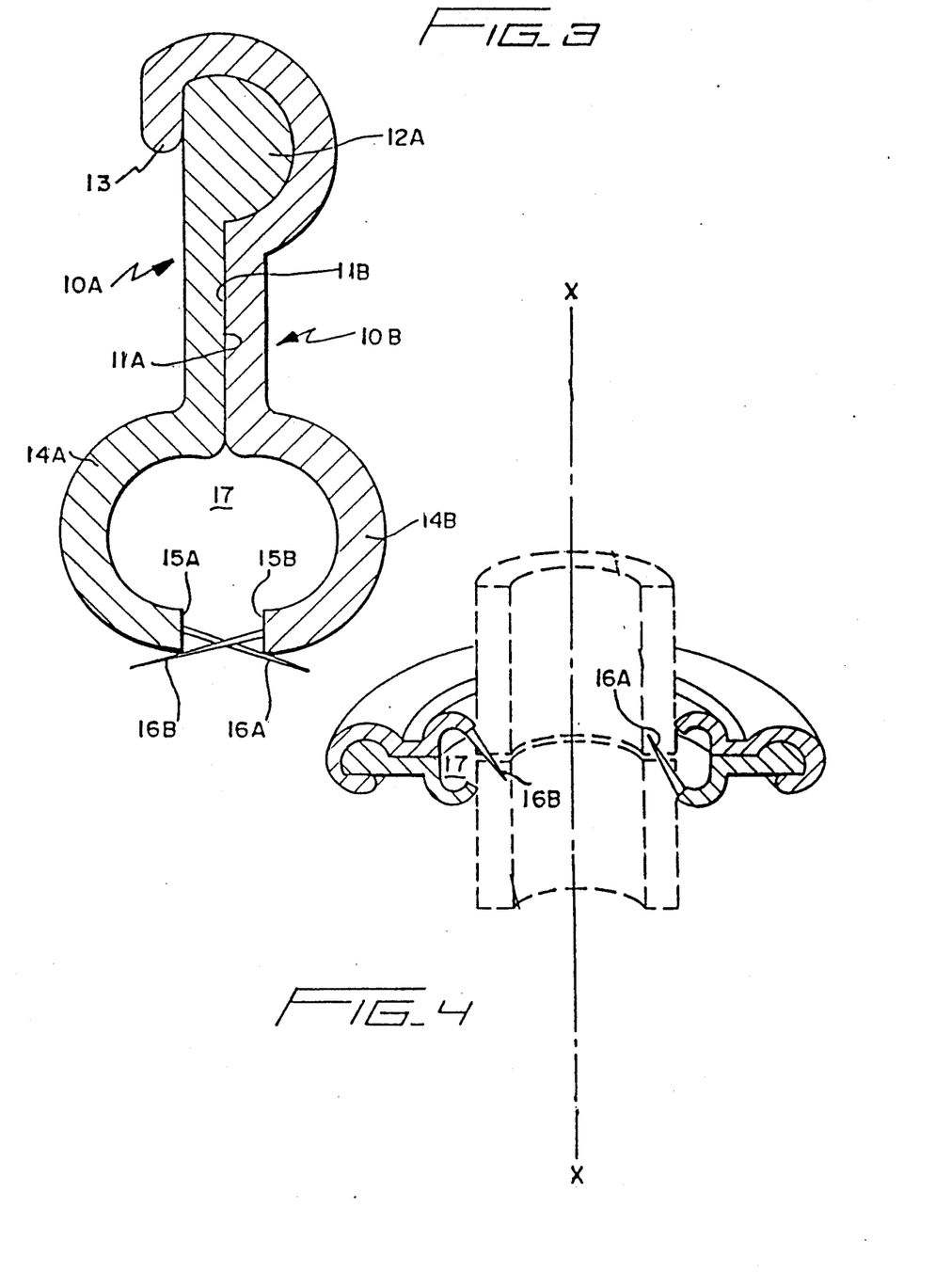
FIG. 3 is a radial cross-section of the first embodiment in operative association.
FIG. 4 shows a diametric cross-section of the first embodiment in association with anastomosed structures shown in broken line.

Male member 10A is configured as an annulus that is elongated in the radial direction which has an inwardly facing, generally planar surface portion 11A on the outer radial extent that operatively associates and abuts with surface 11B of female member 10B; see FIG. 3. An inwardly directed bead element 12A is disposed at the distal end of surface 11A and, in assembly, is adapted to lock into channel 12B of annulus 10B. The channel is formed with a flexible retaining flange 13.

At the proximal periphery of each annulus is a respective inwardly facing channel-forming means 14A, 14B. The free ends of said channel-forming means are shown in the assembly of FIG. 3 as spaced apart end faces 15A, 15B, each face lying outwardly of the plane extended of its respective associated planar surface 11A, 11B. A plurality of retaining pins 16A, 16B are spacedly disposed around the periphery of, and extend inwardly from, each said end face and spacedly alternate with the pins of the opposed series.

As shown in FIG. 4, and easily deducible from the radial section of FIG. 3, the pin lines extended form relatively small angles with the luminal axis x-x in order to maximize the length of organ impalement and to optimally effect pin extension into the opposed organ wall.

Note from FIG. 4 that the assembled device forms a composite channel 17 that bounds the area of organ joinder, that the outer edges of the end faces 15A, 15B abut the organ walls, and that the abutting faces 11A, 11B lend stability to the assembled device and to the spaced relationships thereof.

Thus, with respect to the lumen-forming members, which are illustrated by broken lines, the outflow of blood is inhibited, and the void 17 accommodates any swelling occurring at said area.

Obviously, the annular device will dimensionally vary in accordance with that of the tubular structure treated, and said end faces and pins may be variously configured to effect the aforesaid impalement and organ contact, and the number of and spacing between pins is a matter of mechanical choice and design.

In use of the improved anastomotic device of FIGS. 1A through FIG. 4, a tubular section is inserted through the rear center, or backside, of a first annular member to a predetermined depth and then retracted to effect impalement. A second tubular part is likewise manipulated with respect to the second member. The members are then assembled, as illustrated in FIG. 4, whereupon each pin enters the opposed tubular part to further maintain retention and patency of the lumen.

Figure 5A:
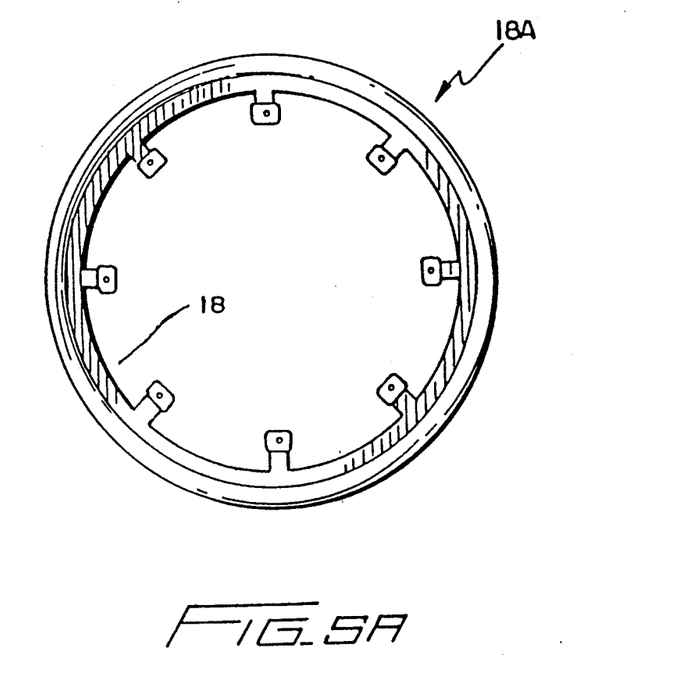
FIGS. 5A and 5B illustrate a second embodiment of the invention.
Figure 5B:
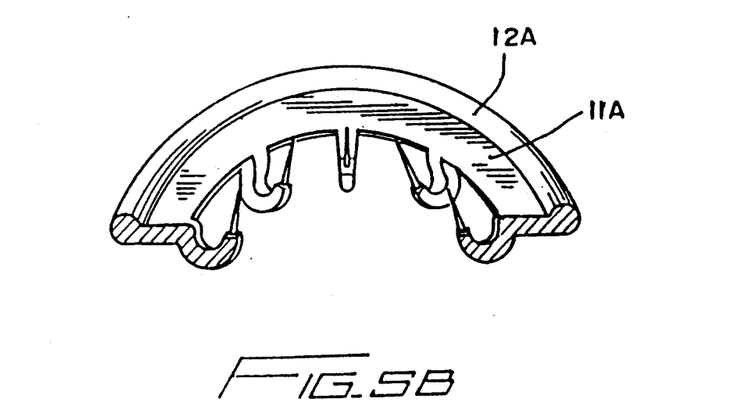

Only a male member 18A is shown in the species of invention illustrated in FIGS. 5A, 5B. This embodiment of the invention is identical to that of FIGS. 1–4, except that the male and female annuli are each slotted, as at 18, between radial sections upon which the retaining pins are mounted; the slots extending from the inner diameters. The depth and width of said slots require only that the radial sections have sufficient rigidity for the tubular retention purpose.

Figure 6:
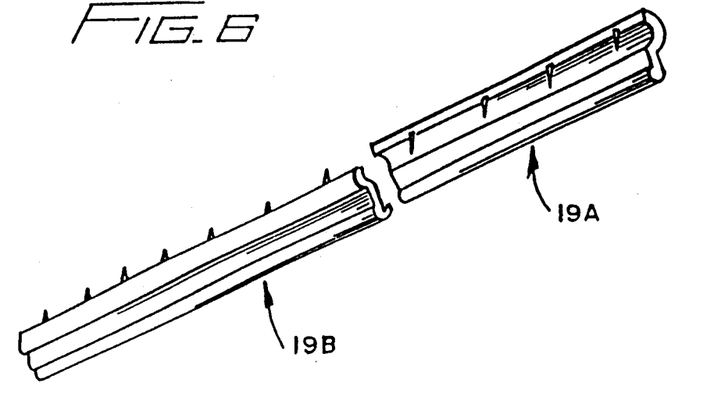
FIG. 6 illustrates a third embodiment of the invention.

The species of invention illustrated in FIG. 6 is identical to that of FIGS. 1A–4, except that the device members are not configured as annuli but are presented as strips 19A, 19B. In use, the male and female strips of predetermined lengths may be assembled with respect to luminal structure or may be utilized to close elongated openings in an anatomical wall.

Figure 7:
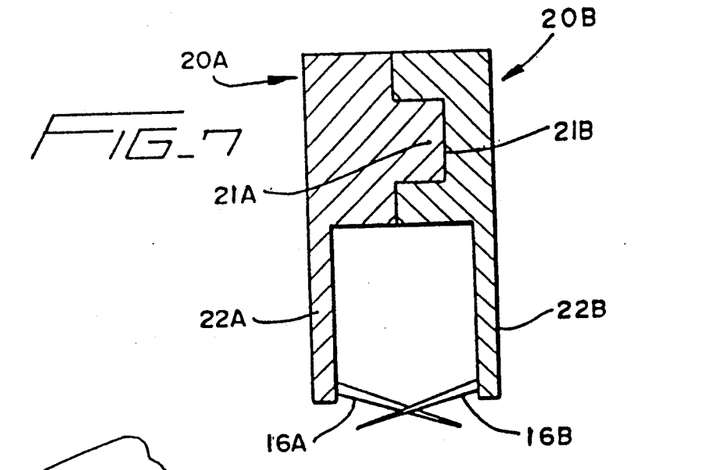
FIGS. 7 and 8 illustrate a fourth embodiment of the invention.
Figure 8:
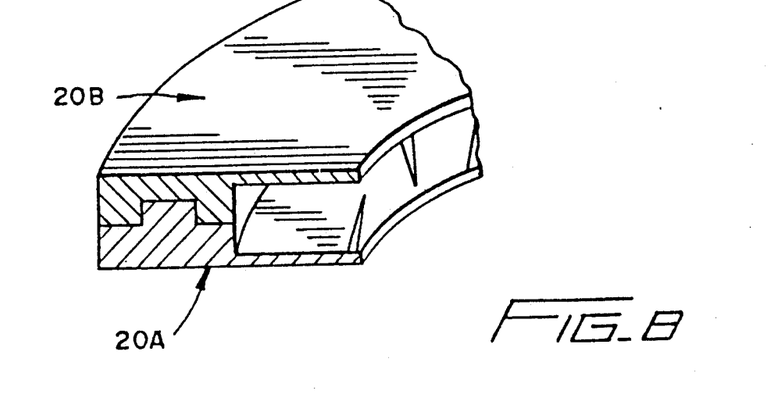

The radial section of FIG. 7 and partial perspective of FIG. 8 illustrate a fourth species of invention that is very similar to that of FIGS. 1A–4, is used in like manner, but is of a more severe design. Thus, male and female annuli 20A and 20B, respectively, are retained in assembly through a frictional fit between a simple annular slot 21B into which is keyed tenon 21A. Element 21A may be continuous. The inwardly extending annular walls of said annuli are simple planar elements 22A, 22B. From the inner peripheries of said planar elements extend pluralities of retaining pins 16A, 16B which are in functional disposition as in FIGS. 1A–4.

Figures 9A, 9B:
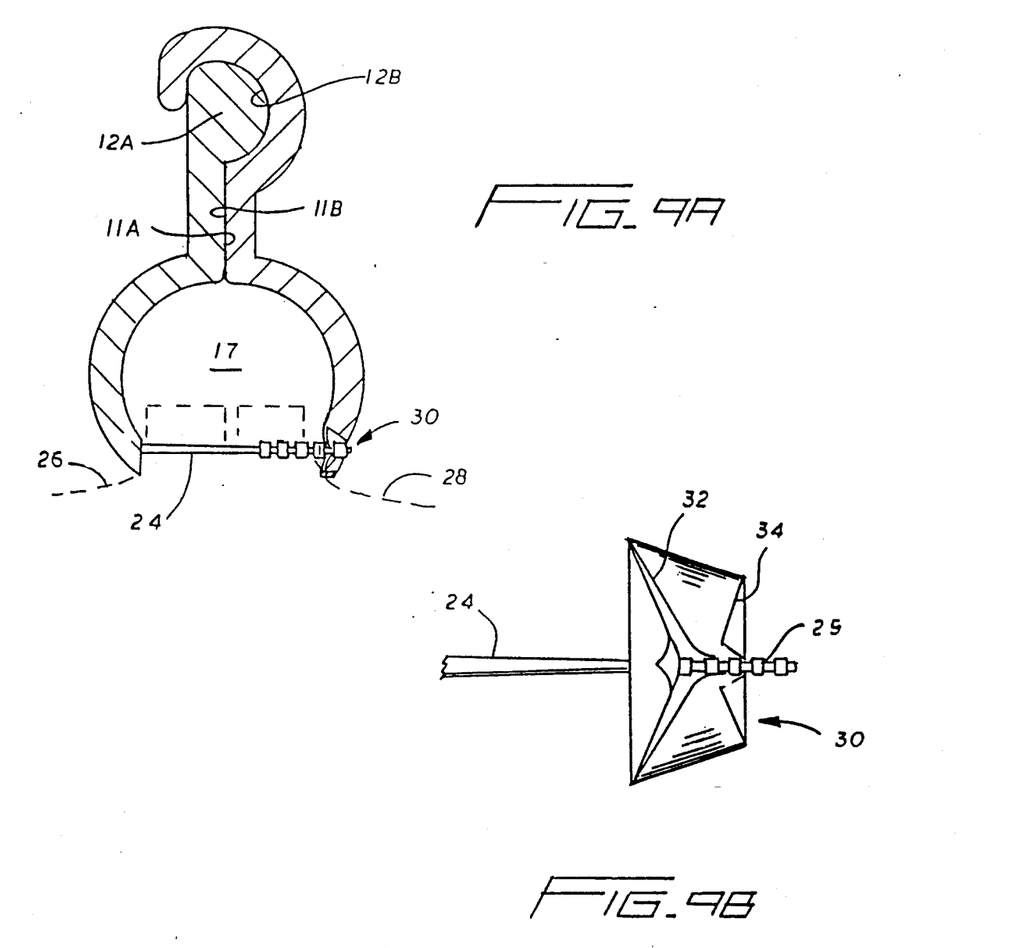
FIGS. 9A and 9B illustrate a fifth embodiment of the invention.

FIG. 9 is a partial radial section of the device and FIG. 9B shows details of the pin and pin securing means. These illustrations are dimensionally exaggerated for purposes of clarity.

Except for said pin and securing means, the radial proximal end section—FIG. 9A structure is substantially that of FIG. 3. However, the overall body structure of the male and female members from which said section is taken may be configured as annuli as in FIGS. 1, 2, 3 or annuli as in FIGS. 5A, 5B or as annuli as in FIGS. 7, 8 or elongated members as in FIG. 6, and each such configuration of structure may be slotted, in the manner of FIGS. 5A, 5B, along the proximal edge of one or both of said male and female members.

Whatever the body configuration of this fifth embodiment of the invention, in functional operative association of said members, pin means 24 projects from a proximal edge face of one member, extends generally normal to the plane extended of the abutting planar surfaces 11A, 11B, through partially everted organ or body parts 26, 28 that are to be joined to effect closure and through securing means 30 formed in a thinned wall portion of the opposed proximal structure of the second member.

As shown in FIG. 9B, pin 24 has a plurality of longitudinally spaced, annular slots or notches 25 which are formed at the distal end thereof and which operatively associate with closure means 30. The latter are comprised of four flexible, triangular panels that are formed by crisscrossed slits 32, 34 formed in said thinned wall portion.

For purposes of clarity, the panels are shown in FIG. 9B in curled disposition. In use, panel edges lie within a selected slot to releasably secure the pin. The selected slot depends on passage of the pin in accordance with desired minimal clamping pressure.

As in all embodiments of the invention, the plurality of pins 24 are spaced along said proximal edge; are each associated with an opposed closure means as described; and in number and spacing therebetween depend primarily on mechanical choice and design. The pins may project from a single one of the male and female members or may alternate with respect to said members.

In use, the partially everted organ or body parts are mounted on pins 24, the pins directed through respective securing means 30, bead element 12A locked in channel 12B and the selected slot 25 then operatively associated with said securing panels whereby to associate the organ or body parts for closure and healing and whereby to avoid an excess of clamping pressure and to inhibit pin withdrawal; the panels of course having adequate flexibility and rigidity for the operative purpose.

It is again pointed out that the male and female members incorporating the novel pin and pin securing means of this fifth embodiment of the invention may be either annuli or elongated, as aforedescribed.

Figure 10A:
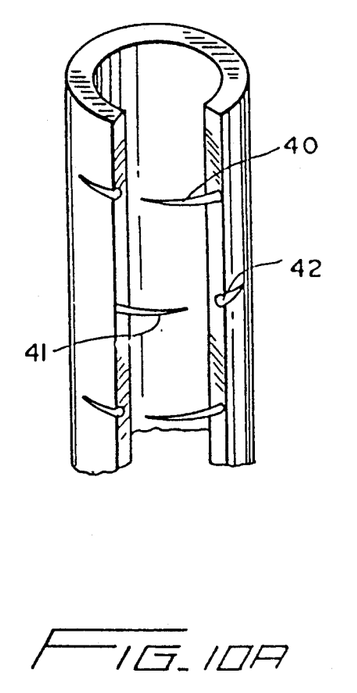
FIGS. 10A and 10B illustrate a sixth embodiment of the invention.
Figure 10B:
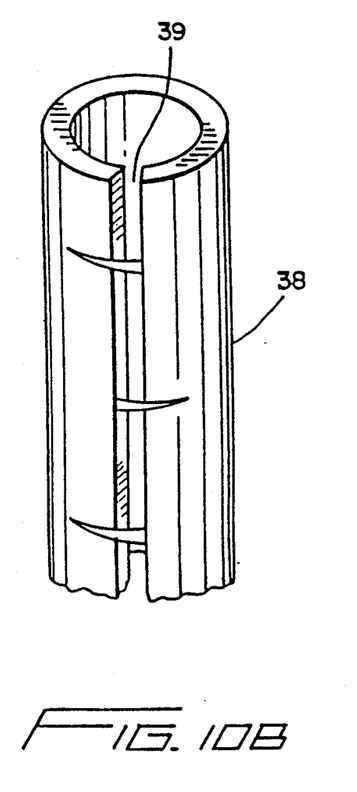

FIGS. 10A, 10B, the sixth embodiment of invention, essentially consist of a tubular member 38 that is linear if intended for closure of an elongated anatomical opening and annular if an anastomotic device. The member is relatively lightly resilient and coextensively slitted as at 39 in a line parallel to its axis or center line. Along each edge defining said slit extend a spaced plurality of retaining pins 40, 41 which extend in the path defined by the tubular structure, and each pin alternates with, and is spaced from, each respective pin that extends from the opposed edge defining such slit.

Further, each said edge is notched 42 up to the extent of receiving therein a respective one of the pins extending from the opposed edge. There may be a light frictional fit between said operatively associated pins and notches.

In use, the tubular device is widened at the slit, the anatomical structures slightly flexed and attached, and the force of widening removed whereat the memory imparted in the tubular device effects closure of same or, if insufficient memory, then the tube is manipulated to effect a retained closure by means of said pins and notches.

The retaining pins may, of course, be configured to lie outside of the tubular path and to enter an anatomical wall and extend into an abutting anatomical wall, as described with respect to foregoing embodiments of the invention.

The materials of fabrication are flexible, compatible with that of the human body, and, where practical, are preferably of an absorbable such as polyglycolic or polylactic materials. Further, such latter materials of fabrication may be treated or coated in order to control the time of material dissolution, as is known in the art.

The embodiments shown and described are only illustrative of the present invention and are not to be construed as definitive thereof; since once apprised of the invention, changes in structure would be readily apparent to one skilled in the art. Hence, the present invention includes all modifications of structure encompassed within the spirit and scope of the following claims.

I claim:

1. Surgical closure means comprising:
   a pair of flexible members;
   means for locking said members into functional association;
   said members being configured to have operatively associated free ends that are removed from said means for locking and are adapted to clamp organ or body parts to be surgically joined for said closure when said members are in said functional association;
   pin means projecting freely from at least one of said free ends and adapted for suturing said organ or body parts for said closure;
   a plurality of longitudinally spaced annular slots formed at the free end portion of said pin means;
   relatively thinned wall means formed in a section of the second of said free ends of the flexible members and adapted to receive said slotted pin portion therethrough when the members are in said functional association;
   means operatively associated with said slot means for securing the pin means with respect to the organ or body parts being sutured and with respect to said second member;
   said securing means being formed in said thinned wall section; and
   said securing means and at least a selected one of the slot means comprising means to control the extent of pressure exerted on the surgically joined organ or body parts by said associated operatively free ends of the flexible members.

2. Surgical closure means as in claim 1, wherein said securing means are flexible panels that are formed by crisscross slits in said thinned wall section and the edges of which engage in said at least one of the annular slots.

3. Surgical closure means as in claim 2, wherein said members are formed as annuli adapted for anastomosis.

4. Surgical closure means as in claim 2, wherein said members are elongated and adapted for closure of a linear wound or opening.

5. Surgical closure means as in claim 2, wherein:
   a portion of each said free end of the flexible members is formed as an inwardly facing channel in a flexible wall; and
   in said functional association of the members, the channels are opposed and form a void that bounds the area of organ or body wall joinder and is adapted to accommodate swelling.

6. Surgical closure means as in claim 5, wherein said members are formed as annuli adapted for anastomosis.

7. Surgical closure means as in claim 5, wherein said members are elongated and adapted for closure of a linear wound or opening 8. Surgical closure means as in claim 5, wherein each said member has a planar surface at an intermediate section thereof and said surfaces abut, when the members are in said functional association, to thereby stabilize such functional association.

9. Surgical closure means as in claim 8, wherein said members are formed as annuli adapted for anastomosis.

10. Surgical closure means as in claim 8, wherein said members are elongated and adapted for closure of a linear wound or opening.

11. Surgical closure means as in claim 8, wherein said means for locking the members into functional association are integrals of the member structures.

12. Surgical closure means as in claim 2, wherein said means for locking the members into functional association are integrals of the member structures.

13. Surgical closure means as in claim 1, wherein each said member has a planar surface at an intermediate section thereof and said surfaces abut, when the members are in said functional association, to thereby stabilize such functional association.

14. Surgical closure means as in claim 13, wherein:
   a portion of each said free end of the flexible members is formed as an inwardly facing channel in a flexible wall; and
   in said functional association of the members, the channels are opposed and form a void that bounds the area of organ or body wall joinder and is adapted to accommodate swelling.

15. Surgical closure means as in claim 1, wherein said means for locking the members into functional association are integrals of the member structures.

* * * * *